US012550235B2

(12) United States Patent
Kühn et al.

(10) Patent No.: US 12,550,235 B2
(45) Date of Patent: Feb. 10, 2026

(54) MICROWAVE HEATING UNIT AND METHOD

(71) Applicant: PHILIP MORRIS PRODUCTS S.A., Neuchatel (CH)

(72) Inventors: Silvio Kühn, Wandlitz (DE); Ralf Dumler, Monthey (CH); Alberto Torreño Núñez, Lustenau (AT)

(73) Assignee: PHILIP MORRIS PRODUCTS S.A., Neuchatel (CH)

( * ) Notice: Subject to any disclaimer, the term of this patent is extended or adjusted under 35 U.S.C. 154(b) by 922 days.

(21) Appl. No.: 17/616,309

(22) PCT Filed: May 27, 2020

(86) PCT No.: PCT/EP2020/064699
§ 371 (c)(1),
(2) Date: Dec. 3, 2021

(87) PCT Pub. No.: WO2020/244996
PCT Pub. Date: Dec. 10, 2020

(65) Prior Publication Data
US 2022/0330396 A1 Oct. 13, 2022

(30) Foreign Application Priority Data
Jun. 6, 2019 (EP) .................................... 19178687

(51) Int. Cl.
*H05B 6/80* (2006.01)
*A24F 40/10* (2020.01)
(Continued)

(52) U.S. Cl.
CPC ............... *H05B 6/80* (2013.01); *A24F 40/10* (2020.01); *A24F 40/42* (2020.01); *A24F 40/46* (2020.01);
(Continued)

(58) Field of Classification Search
CPC .......... A24F 40/10; A24F 40/20; A24F 40/42; A24F 40/46; A61K 31/352; A61K 9/007;
(Continued)

(56) References Cited

U.S. PATENT DOCUMENTS 9,980,518 B1 * 5/2018 Most .................... H05B 1/0244
2003/0205571 A1 11/2003 Flugstad et al.
(Continued)

FOREIGN PATENT DOCUMENTS

CN 1545823 A 11/2004
CN 100336577 C 9/2007
(Continued)

OTHER PUBLICATIONS

International Search Report and Written Opinion dated Jul. 20, 2020 from counterpart International Patent Application No. PCT/EP2020/064699.
(Continued)

*Primary Examiner* — Ibrahime A Abraham
*Assistant Examiner* — Joe E Mills, Jr.
(74) *Attorney, Agent, or Firm* — Oblon, McClelland, Maier & Neustadt, L.L.P.

(57) ABSTRACT

A microwave heating component is provided, including a sample holding and exposing component to receive and hold a sample in a holding and exposing space and to expose the sample to a microwave radiation field within the space; a microwave radiation component including a microwave radiation source or radiation signal source, the microwave radiation component to supply the field and/or a signal to the space; and an impedance matching component to achieve impedance matching between the space and the radiation signal and/or the field and including electrodes for generating the field upon receipt of the signal, the microwave heating component being configured for heating an aerosol-
(Continued)

Figure 1:
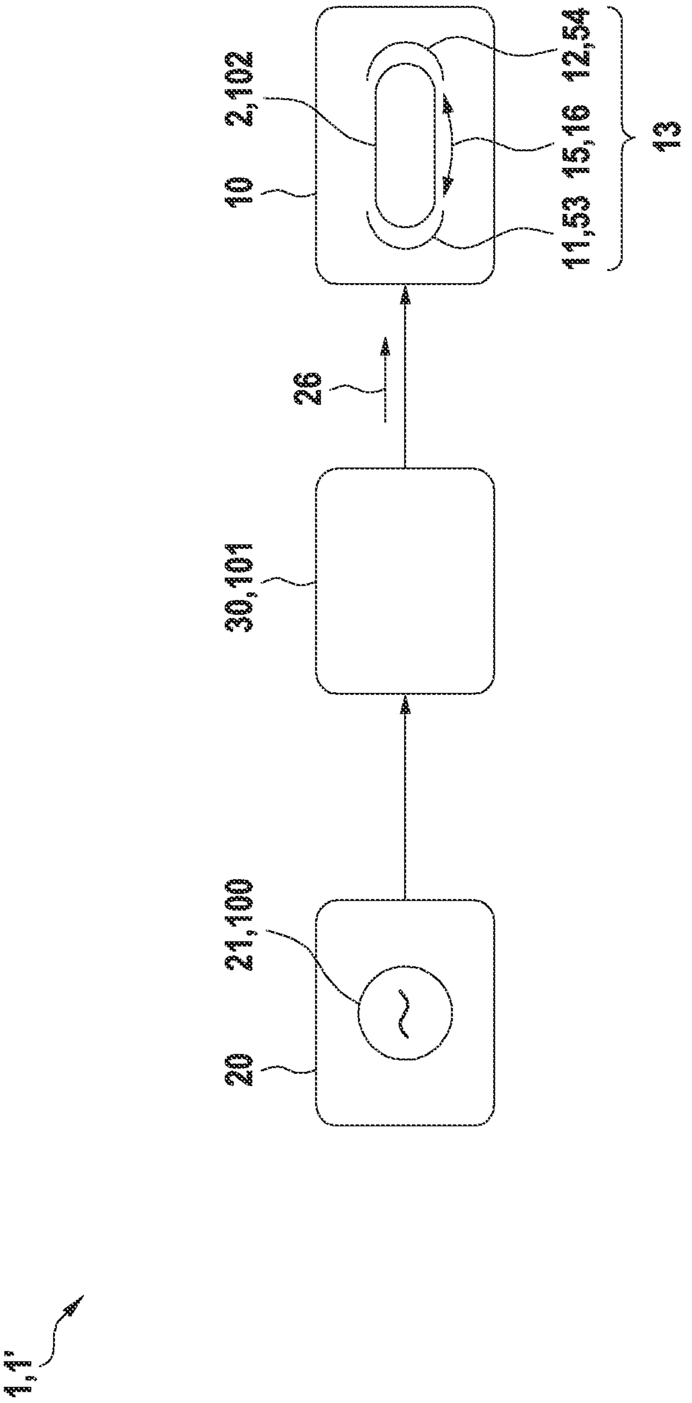

forming sample due to microwave absorption by a material of the sample thereby releasing by or from the sample upon heating the sample at least one aerosol, in or as an inhalation, vaporizer, and/or smoking product or device and/or for pulmonary drug delivery.

16 Claims, 12 Drawing Sheets

(51) Int. Cl.

| | |
|---|---|
| ***A24F 40/42*** | (2020.01) |
| ***A24F 40/46*** | (2020.01) |
| ***A61K 9/00*** | (2006.01) |
| ***H05B 6/66*** | (2006.01) |
| ***H05B 6/68*** | (2006.01) |

(52) U.S. Cl.
CPC ............ *A61K 9/007* (2013.01); *H05B 6/664* (2013.01); *H05B 6/68* (2013.01)

(58) Field of Classification Search
CPC ........... A61M 11/042; A61M 15/0036; A61M 15/06; A61M 2205/3368; A61M 2205/3686; A61M 2205/50; A61M 2205/7545; A61M 2205/8206; H05B 6/664; H05B 6/68; H05B 6/80
See application file for complete search history.

(56) References Cited

U.S. PATENT DOCUMENTS

| | | | |
|---|---|---|---|
| 2011/0139773 | A1 | 6/2011 | Fagrell et al. |
| 2016/0338154 | A1 | 11/2016 | Nagahisa |
| 2018/0228217 | A1 | 8/2018 | Mironov et al. |
| 2018/0261432 | A1 | 9/2018 | Ashida |
| 2019/0037925 | A1 | 2/2019 | Hon et al. |
| 2019/0356047 | A1 | 11/2019 | Guduru |

FOREIGN PATENT DOCUMENTS

| | | | |
|---|---|---|---|
| CN | 100593982 | C | 3/2010 |
| CN | 103315404 | A | 9/2013 |
| CN | 103315405 | B | 8/2015 |
| CN | 206227716 | U | 6/2017 |
| CN | 108552613 | A | 9/2018 |
| CN | 108777893 | A | 11/2018 |
| CN | 109567275 | A | 4/2019 |
| CN | 109640717 | A | 4/2019 |
| CN | 1103133636 | A | 10/2019 |
| CN | 209768992 | U | 12/2019 |
| CN | 111789302 | B | 8/2024 |
| CN | 110859323 | B | 11/2024 |
| EP | 1639862 | A1 | 3/2006 |
| EP | 3481148 | A1 | 5/2019 |
| FR | 1044857 | | 11/1953 |
| JP | 11-123758 | A | 5/1999 |
| JP | 4002276 | B2 | 10/2007 |
| JP | 2013514608 | A | 4/2013 |
| JP | 2017-170480 | A | 9/2017 |
| JP | 2018148499 | A | 9/2018 |
| JP | 2018-537077 | A | 12/2018 |
| KR | 10-1951762 | B1 | 2/2019 |
| KR | 102167498 | B1 | 10/2020 |
| KR | 102178423 | B1 | 11/2020 |
| KR | 102214675 | B1 | 2/2021 |
| WO | WO 03/019985 | A1 | 3/2003 |
| WO | 2007007123 | A1 | 1/2007 |
| WO | WO 2020/079811 | | 4/2010 |
| WO | WO 2012/003827 | A2 | 1/2012 |
| WO | WO 2017/143515 | A1 | 8/2017 |
| WO | WO 2018/114849 | A1 | 6/2018 |
| WO | 2018169600 | A1 | 9/2018 |
| WO | 2018172962 | A2 | 9/2018 |
| WO | WO 2020/079812 | | 4/2020 |

OTHER PUBLICATIONS

European Search Report dated Nov. 21, 2019 from counterpart European Patent Application No. 19178687.0.
Chinese Office Action issued Jan. 12, 2024 in Chinese Patent Application No. 202080041390.0 (with English Translation), 11 pages.
Japanese Office Action dated Oct. 10, 2023 from counterpart Japanese Patent Application No. 2015-570884.
Chinese Office Action issued Jun. 28, 2024 in Chinese Patent Application No. 202080041390.0 (submitting English Translation of Office Action only), 7 pages.
Japanese Office Action issued Dec. 3, 2024 in Japanese Patent Application No. 2024-026688 (with unedited computer-generated English Translation), 10 pages.
Canadian Office Action issued Jan. 29, 2025 in Canadian Patent Application No. 3,142,259, 4 pages.
European Office Action issued Mar. 3, 2025 in European Patent Application No. 2072733.5, 18 pages.
Notice of Allowance issued Dec. 23, 2024, in corresponding Korean Patent Application No. 10-2021-7039820 (with English Translation), 4 pages.
Japanese Decision to Grant issued Mar. 18, 2025 in corresponding Japanese Patent Application 2024-026688, with English Machine Translation, 4 pages, citing documents 1 and 15-17 therein.
European Office Action issued Apr. 23, 2025 in corresponding European Patent Application No. 20 727 333.5, 4 pages.

* cited by examiner

MICROWAVE HEATING UNIT AND METHOD

This application is the National Phase of International Application PCT/EP2020/064699 filed May 27, 2020 which designated the U.S.

This application claims priority to European Patent Application No. 19178687.0 filed Jun. 6, 2019, which application is incorporated by reference herein.

The present invention refers to microwave heating units and methods which are in particular configured for heating an aerosol-forming sample due to microwave absorption by a material of the sample and in particular for thereby releasing by or from said sample upon heating said sample at least one aerosol and/or in a or as a inhalation, vaporizer and/or smoking product or device, in particular for medical and/or pulmonary drug delivery applications.

There are devices as consumer products known, for instance such as E-cigarettes or the like, which are configured in order to release an aerosol from a sample due to heating. However, these known devices suffer from incomplete, non-uniform and/or comparable slow heating of the sample. Accordingly, the required temperature and/or temperature distribution cannot be achieved for realizing a suitable heating process in order to serve all the consumers requirements.

It is an object underlying the present invention to provide alternative microwave heating units and methods which have improved heating and thus aerosol releasing capabilities.

The object underlying the present invention is achieved by microwave heating unit according to independent claim 1 and by a microwave heating method according to independent claim 12. Preferred embodiments are defined in the respective dependent claims.

According to a first aspect of the present invention a microwave and/or RF (radio frequency) heating unit for heating an aerosol-forming sample due to microwave and/or RF absorption by a material of the sample and in particular for thereby releasing by or from said sample upon heating said sample at least one aerosol is provided, in particular in a or as a inhalation, vaporizer and/or smoking product or device, in particular for pulmonary drug delivery.

The microwave and/or RF heating unit according to the present invention comprises:

- (i) a sample holding and exposing unit configured to receive and hold a sample in a holding and exposing space and to expose the sample to a microwave radiation field within said holding and exposing space,
- (ii) a microwave radiation and/or RF unit configured to supply the microwave and/or RF radiation field and/or an underlying microwave and/or RF radiation signal to said holding and exposing space, and at least one of

- (iii) an impedance matching unit configured to achieve impedance matching between the holding and exposing space and the microwave and/or RF radiation field and/or the underlying microwave and/or RF radiation signal and
- (iv) a free running oscillator which is configured to generate, and supply said microwave and/or RF radiation field and/or said underlying microwave and/or RF radiation signal.

By these measures a comparable high degree of reliability of the heating process can be achieved, in particular in terms of rapidity, uniformity and/or completeness. This is in particular achieved by means of a contactless and/or non-the resistive heating process underline the invention's microwave heating unit and method.

According to a preferred embodiment of the invention's microwave heating unit said sample holding and exposing unit comprises a sample holder defining and forming said holding and exposing space within an interior, in particular as a cavity, by means of first and second holding portions and/or first and second holding portions separated by a slit structure.

Advantageously the impedance matching unit and in particular an impedance matching network thereof is or are tunable in its matching properties concerning at least one of impedance, frequency and the aerosol-forming sample. By these measures the effectiveness and/or uniformity of the microwave heating process can be further improved.

The impedance matching unit and in particular an impedance matching network thereof may comprise at least one of

- electrodes for generating the microwave radiation field upon receipt of an underlying microwave radiation signal and/or which geometrically fit to the aerosol-forming sample, holding and exposing space and/or a or the cavity thereof,
- an output which contains waveguide structures, transmission lines and/or stubs,
- $\frac{1}{8}\lambda$ to $\frac{1}{4}\lambda$ wave guide matching elements, wherein $\lambda$ denotes the wavelength of the underlying microwave radiation, and
- one or plural dielectric material portions, by means of which the impedance matching unit is in particular tunable in its properties.

Further additionally or alternatively the microwave radiation unit may be or may comprise one or plural microwave radiation sources and/or microwave radiation signal sources, in particular in the form of solid-state microwave sources or and/or microwave radiation signal sources, respectively.

Further additionally or alternatively a connecting configuration regarding such one or plural microwave radiation sources and/or microwave radiation signal sources may be provided, set connecting configuration having a connector and/or a waveguide for providing connection to the respective source.

Said one or plural microwave radiation (signal) sources and/or solid-state microwave (signal) sources may be configured such that upon energization they are capable of generating and/or releasing said underlying microwave radiation field and/or said microwave radiation field signal.

Accordingly, a power source unit may be provided which is configured in order to energize the underlying microwave radiation unit and in particular the one or plural microwave radiation (signal) sources and which in particular comprises one or plural DC power sources.

Said microwave radiation unit and in particular a microwave radiation (signal) source thereof may be or may comprise a transistor amplifier.

The impedance matching unit and in particular an impedance matching network thereof may be or may comprise a microwave feedback port and/or a microwave signal feedback port which is connected to an input of the transistor amplifier in order to meet an underlying oscillation condition.

Under such circumstances it is of particular advantage if an additional smart phase and/or an amplitude correction device is or are connected in between the feedback port and the input of the transistor amplifier.

The microwave radiation generating and/or releasing unit and in particular a microwave source thereof may be or may comprise a transistor amplifier and in particular may have an input that is connected to an output of a low power signal source.

Under such circumstances the low power signal source may be or may comprise at least one of a phased locked loop (PLL), a voltage-controlled oscillator (VCO) and a direct digital synthesis (DDS).

A Microwave and/or RF heating unit according to the present invention may be configured in order to at least one of process an aerosol-forming sample which is formed as or comprises at least one of a liquid substance, a solid substance, a medical *Cannabis* containing substance, a nicotine containing substance, a phyto-active substance, a botanical drug substance, a pharmaceutical active substance and a tobacco substance, and to release said at least one aerosol comprising at least one of a phyto-active substance, botanical drug substance and a pharmaceutical active ingredient.

In distinct concrete embodiments, the invention's microwave heating unit may be formed in or as at least one of an a drug delivery product and/or device, inhalation product and/or device, smoking product and/or device, a mobile product and/or device and/or a portable product and/or device.

According to a further alternative or additional preferred embodiment of the invention's microwave and/or RF heating unit the underlying free running oscillator at least one of is connected to the sample holding and exposing unit or is a part thereof, is, comprises and/or realizes an IQ modulator and/or the functionality of an IQ modulator which means the ability of controlling the phase and/or the gain and comprises within a feedback loop a or the transistor amplifier, an or the impedance matching unit and/or impedance matching network and a or the amplitude/phase correction device.

The operation and thus the oscillation process of the free running oscillator is initiated by the statistical and/or stochastic properties and in particular by noise of the overall electric circuit. Amplitude, phase and gain properties are defined by the electric properties of the further components and/or geometry and material portions of the sample, the sample holding and exposing means and in particular the sample holder with the holding and exposing space and in particular the cavity and the impedance matching unit and network, for instance the slit structure and any dielectric.

In general and in an initial stage of the oscillation process, all frequency components are contained according to its ratio within the noise spectrum. However and based on the further properties of the entire circuit and in particular of an employed face an amplitude correction device, the required signal can be obtained in amplified formed by and according feedback process.

In this regard, the phase and amplitude correction device is able to shift the overall phase response as well as the overall gain of the amplifier or amplifier chain and resonant impedance matching to meet the phase and amplitude condition at desired frequency to make the circuit to an oscillator. A slight tuning of frequency of oscillation is possible by change the phase part. With adjusting the overall gains amplitude, the second mayor oscillation condition is controllable and needs to meet at small signal condition a gain of at least one. It can be used for power and efficiency control.

Of course, the impedance matching unit and network and the properties are of importance, too:

In general a high electrical field at the given frequency is required to heat up the sample dielectrically. When using signals at low frequency, transformers and/or lumped elements like capacitors and inductors/coils building resonant circuits which can be used to match the generator output impedance to the high impedance behavior of the electrodes for dielectric heating of the sample. The electrical loss of the sample material given by its tan(δ) property does provide the real part of the impedance and causes heating of the sample when inserting electrical fields.

At higher frequencies it is more suitable to use transmission lines and waveguides to match electrodes and signal source. Which means increase the voltage amplitude of the source output. The electrodes of the holding structure have a slightly capacitive impedance cause of its geometry, e.g. in the order of magnitude of 100 fF. A transmission line—e.g. as a part of the impedance matching unit 30, namely 30*a*) with a length of about ⅛λ to about ⅕λ transforms it to lower capacitive impedance which is equivalent to higher capacitance. When connecting a coil or the short circuit with a short waveguide less the $1/10$λ at this point, the inductive and capacitive part compensate each other and build a resonance circuit. This type of impedance matching transforms the electrical losses of the sample into a suitable impedance range for microwave signal sources e.g. transistor output stages.

The present invention further relates to microwave and/or RF (radio frequency) heating method for heating an aerosol-forming sample due to microwave absorption by a material of said sample and in particular for thereby releasing by or from said sample upon heating said sample at least one aerosol, the at least one aerosol comprising at least one of a phyto-active substance and a pharmaceutical active ingredient, wherein a microwave heating unit according to any one of the preceding claims is used for heating said sample.

Different entities may be used and/or heated as a sample and/or as a part thereof, e.g.:

an aerosol-forming substrate of a smoking article, in particular of a nicotine and/or non-nicotine containing smoking article, a tobacco-loaded solid-aerosol forming sample of a smoking sample, in particular of a nicotine and/or non-nicotine containing smoking sample, an aerosol-forming substrate with or of a nicotine and/or non-nicotine containing liquid, an aerosol-forming active pharmaceutical ingredient, an aerosol-forming phyto-active substance and in particular from raw plant material and/or from a plant material, an aerosol-forming delta-9-Tetrahydrocanabinol (THC) and/or cannabidiol (CBD) and/or cannabinoids containing plant material, an aerosol-forming botanical drug substance and/or a botanical drug product, and/or an aerosol-forming substrate having at least one of microwave sensitizers and/or absorbers of the group of substances which comprises functionalized polysilsesquioxanes, carbon nanotubes, graphite, graphene, activated carbon, activated charcoal, metal powder, semiconductor powder and combinations and mixtures thereof, or any of their combinations.

In order to achieve a higher microwave efficiency, materials referred to herein as sensitizers may be a part of or may be mixed with the aerosol-forming material at low concentrations in order to significantly increase the local dielectric loss. When exposed to microwave energy, the sensitizer creates uniform heating of the aerosol forming material and increase efficiency of heating.

Preferably, a temperature of the aerosol-forming sample is measured or/and approximated and a value of which may be fed to a temperature control loop unit configured for controlling power supplied for energizing a microwave generation and/or releasing process.

It is of particular advantage to have an operation frequency which within a range of about 1 MHz to about 15 GHz, preferably in an ISM band, in a range of about 2.4 GHz to about 2.5 GHz and/or with a center frequency of about 2.45 GHz.

An underline operation power in continuous mode may be in a range from about 0.1 mW to 50 Watt and preferably around about 2 W.

Additionally or alternatively, an operation power in a pulsed mode may be in a range from about 0.1 mW to about 50 W and preferably around about 3 W.

An operation power may be ramped up between a value of about 0.1 W and a value of about 30 W.

As a further additional or alternative embodiment, an operation frequency may be set to a constant value.

An operation frequency may also be varied with time and in particular swept between a minimum value and the maximum value, in particular between about 2.4 GHz and about 2.5 GHz.

According to preferred embodiments of the present invention, an aerosol-forming sample may be used that is formed as, comprise, may be contained inside and/or may be packed inside at least one of a fluid material, a solid material, a tablet, capsule, cartridge, shell vial, pellet and/or can be fitted according to the size of an underlying cavity and/or pharmaceutical excipients are added to the aerosol-forming sample.

Further alternatively or additionally, said aerosol-forming sample may be or may form a vessel and/or may have a housing, wherein the housing in particular may be transparent with respect to microwave radiation, may comprise or may be formed of plastic, synthetic material, poly-propylene, glass, quartz and/or has a comparable low dielectric loss factor ε" and/or a comparable low loss tangent tan(δ).

As a further alternative or additional embodiment of the present invention, underlying capsule, cartridge or the like may be formed of or may comprise glass or quartz, in particular comprising ITO (indium tin oxide) at its ends, as ITO is electrically conducting and may therefore supply the high-frequency or microwave signal to the interior of the capsule. Said capsule may further in such an arrangement comprise 2 through holes with a ceiling in order to allow a gas stream or airstream to flow therethrough for releasing the aerosol generated from the inside.

Said aerosol-forming sample may be contained in a vessel formed as a mouthpiece which is configured for allowing inhalation of the formed aerosol, as an integral piece, as a disposal and/or to comprise a filter, in particular with the low or very low particulate filtration efficiency, and/or a hollow tube.

According to preferred embodiments of the present invention a plant-based material may be used which may be selected from the group comprising *Cannabis sativa, Cannabis indica, Cannabis ruderalis, Acacia* spp, *Amanita muscaria, Yage, Atropa belladonna, Areca catechu, Brugmansia* spp., *Brunfelsia latifolia, Desmanthus illinoensis, Banisteriopsis caapi, Trichocereus* spp., *Theobroma cacao, Capsicum* spp., *Cestrum* spp., *Erythroxylum coca, Solenostemon scutellarioides, Arundo donax, Coffea arabica, Datura* spp., *Desfontainia* spp., *Diplopterys cabrerana, Ephedra sinica, Claviceps purpurea, Paullinia cupana, Argyreia nervosa, Hyoscyamus niger, Tabernanthe iboga, Lagochilus inebriens, Justicia pectoralis, Sceletium tortuosum, Piper methysticum, Catha edulis, Mitragyna speciosa, Leonotis leonurus, Nymphaea* spp., *Nelumbo* spp., *Sophora secundiflora, Mucuna pruriens, Mandragora officinarum, Mimosa tenuiflora, Ipomoea violacea, Psilocybe* spp., *Panaeolus* spp., *Myristica fragrans, Turbina corymbosa, Passiflora incarnata, Lophophora williamsii, Phalaris* spp., *Duboisia hopwoodii, Papaver somniferum, Psychotria viridis*, spp., *Salvia divinorum, Combretum quadrangulare, Trichocereus pachanoi, Heimia salicifolia, Stipa robusta, Solandra* spp., *Hypericum perforatum, Peganum harmala, Tabernaemontanaspp, Camellia sinensis, Nicotiana tabacum, rusticum, Virola theidora, Voacanga africana, Lactuca virosa, Artemisia absinthium, Ilex paraguariensis, Anadenanthera* spp., *Corynanthe yohimbe, Calea zacatechichi, Coffea* spp. (*Rubiaceae*), a *Sapindaceae, Camellia* spp., *Malvaceae* spp., *Aquifoliaceae* spp., *Hoodia*, spp. *Chamomilla recutita, Passiflora incarnate, Camellia sinensis, Mentha piperita, Mentha spicata, Rubus idaeus, Eucalyptus globulus, Lavandula officinalis, Thymus vulgaris, Melissa officinalis, Aloe Vera, Angelica, Anise, Ayahuasca* (*Banisteriopsis caapi*), Barberry, Black Horehound, Blue Lotus, Burdock, Camomille/Chamomile, Caraway, Cat's Claw, Clove, Comfrey, Corn Silk, Couch Grass, Damiana, Damiana, Dandelion, *Ephedra, Eucalyptus*, Evening Primrose, Fennel, Feverfew, Fringe Tree, Garlic, Ginger, Ginkgo, Ginseng, Goldenrod, Goldenseal, Gotu Kola, Green Tea, Guarana, Hawthorn, Hops, Horsetail, Hyssop, Kola Nut, Kratom, Lavender, Lemon Balm, Licorice, Lion's Tail (Wild Dagga), Maca Root, Marshmallow, Meadowsweet, Milk Thistle, Motherwort, Passion Flower, Passionflower, Peppermint, Prickly Poppy, Purslane, Raspberry Leaf, Red Poppy, Sage, Saw Palmetto, Sida Cordifolia, Sinicuichi (Mayan Sun Opener), Spearmint, Sweet Flag, Syrian Rue (*Peganum harmala*), Thyme, Turmeric, Valerian, Wild Yam, Wormwood, Yarrow, Yerba Mate, Yohimbe, *Cannabis sativa, Cannabis indica*, and *Cannabis ruderalis*, any part and/or any combination thereof.

Additionally or alternatively a sample may be used which comprises and/or is capable of releasing a pharmacologically active agent of the sample and/or of the aerosol released is selected from the group comprising A9-tetrahydrocannabinol (THC), cannabidiol (CBD), cannabigerols (CBG), cannabichromenes (CBC), cannabinol (CBN), cannabinodiol (CBDL), cannabicyclol (CBL), cannabielsoin (CBE), cannabidivarin (CBDV), tetrahydrocannabivarin (THCV), cannabitriol (CBT) and combinations and parts thereof.

According to further additional or alternative preferred embodiments of the present invention within the inventions microwave heating method a sample may be used which comprises and/or is capable of releasing one or plural flavorants and/or sensates, said one or plural flavorants and/or sensates configured to generate taste and/or aroma, including any natural or synthetic flavorant, such as tobacco, smoke, menthol, mint, such as peppermint and spearmint, chocolate, licorice, citrus and other fruit flavorants, gamma octalactone, vanillin, ethyl vanillin, breath freshener flavorants, spice flavorants such as cinnamon, methyl salicylate, linalool, bergamot oil, geranium oil, lemon oil, and ginger oil, flavorant compounds selected from the group comprising of an acid, an alcohol, an ester, an aldehyde, a ketone, a pyrazine, combinations thereof and equivalents, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-valeric acid, combinations thereof and equivalents, in encapsulated form for controlled delivery, peppermint, spearmint, wintergreen, menthol, cinnamon, chocolate, vanillin, licorice, clove, anise, sandalwood, geranium, rose oil, vanilla, lemon oil, cassia, spearmint, fennel, ginger, ethylacetate, isoamylacetate, propylisobutyrate, isobutylbutyrate, ethylbutyrate, ethylvalerate, benzylformate, limonene, cymene, pinene, linalool, geraniol, citronellol, citral, peppermint oil, orange oil, coriander oil, borneol, fruit extract, and equivalents. In a preferred embodiment, essential oils and essences of coffee, tea, cacao, and mint, a suitable amount of a flavorant present in core ranges from about 0.001 wt % to about 50 wt %, from about 1 wt % to about 40 wt %, from about 10 wt % to about 30 wt %, flavorant incorporated as a solid powder, sprayed dried as a liquid, or mixed with starch or gum-type matrix, and/or wherein any sensate is formed as or comprises one or plural an ingredients configured to order to induce a sensorial experience, such as tingling, sensation of warmth, sensation of cooling, and equivalents, and is or comprises at least one of an acetic acid, adipic acid, citric acid, lactic acid, maleic acid, succinic acid, tartaric acid, equivalents and mixtures thereof, with a suitable amount of a sensate agent in ranges of about 0.001 wt % to about 5 wt %, preferably of about 0.1 wt % to about 2 wt %, and/or their arbitrary combinations.

A sample may be used which comprises of tobacco, tobacco extracts and tobacco capsules, any raw or processed form of tobacco, as a powder, as a dust, a granule, a shred, a slurry, a flowable gel and equivalents, in particular with a final tobacco concentration ranging from 1 wt. % to 99 wt. % of a final composition and/or at most from about 10%, 15%, 20%, 25%, 30%, 35%, 40%, 45%, 50%, 55%, 60%, 65%, 70%, 75%, 80%, 85%, or 90% tobacco and/or one of the arbitrary combinations.

According to other preferred embodiments of the invention's microwave heating method sample may be used which comprises one or plural of humectants for maintaining and/or protecting moisture levels of the sample material and in particular of tobacco material in tobacco-containing hydrogel capsules and/or as preservatives to remove excess water and thereby, reduce the growth of micro-organisms, to provide a higher moisture feel in a drier sample material, tobacco material, tobacco substitute material and/or a drier smokeless tobacco material, comprising one or plural of glycerol and propylene glycol and/or in ranges from about 0.001 wt. % to about 5 wt. %, from about 0.1 wt. % to about 2 wt. %, and/or their arbitrary combinations.

According to other additional or alternative preferred embodiments of the invention's microwave heating method, a sample may be used which comprises a liquid, selected from the group of polyhydric alcohols consisting of glycerin, propylene glycol, and combinations thereof.

In the following, further alternative or additional preferred embodiments of the present invention in view of the involved aerosol-forming sample and the underlying material of the sample are presented:

An ingredient of the aerosol-forming sample and/or of the underlying material of the sample may comprise a drug of the composition of one of the following classes: antibiotics, anticonvulsants, antidepressants, antiemetics, antihistamines, antiparkinsonian drugs, antipsychotics, anxiolytics, drugs for erectile dysfunction, drugs for migraine headaches, drugs for the treatment of alcoholism, drugs for the treatment of addiction, muscle relaxants, nonsteroidal anti-inflammatories, opioids, other analgesics and stimulants.

Where the drug is an antibiotic, may be selected from one of the following compounds: cefmetazole; cefazolin; cephalexin; cefoxitin; cephacetrile; cephaloglycin; cephaloridine; cephalosporins, such as cephalosporin C; cephalotin; cephamycins, such as cephamycin A, cephamycin B, and cephamycin C; cepharin; cephradine; ampicillin; amoxicillin; hetacillin; carfecillin; carindacillin; carbenicillin; amylpenicillin; azidocillin; benzylpenicillin; clometocillin; cloxacillin; cyclacillin; methicillin; nafcillin; 2pentenylpenicillin; penicillins, such as penicillin N, penicillin O, penicillin S, penicillin V; chiorobutin penicillin; dicloxacillin; diphenicillin; heptylpenidillin; and metampicillin.

Where the drug is an anticonvulsant, it may be selected from one of the following compounds: gabapentin, tiagabine, and vigabatrin.

Where the drug is an antidepressant, it may be selected from one of the following compounds: amitriptyline, amnoxapine, benmoxine, butriptyline, clomipramine, desipramine, dosulepin, doxepin, imipramine, kitanserin, lofepramine, medifoxamine, mianserin, maprotoline, mirtazapine, nortriptyline, protriptyline, trimipramine, viloxazine, citalopram, cotinine, duloxetine, fluoxetine, fluvoxamine, milnacipran, nisoxetine, paioxetine, reboxetine, sertraline, tianeptine, acetaphenazine, binedaline, brofaromine, cericlamine, clovoxamine, iproniazid, isocarboxazid, moclobemide, phenyhydrazine, pheneizine, selegiline, sibutramine, tranylcypromine, ademetionine, adrafinil, amesergide, amnisuipride, amperozide, benactyzine, bupropion, caroxazone, gepirone, idazoxan, metralindole, milnacipran, minaprine, nefazodone, noinifensine, ritanserin, roxindole, Sadenosylmethionine, tofenacin, trazodone, tryptophan, venlafaxine, and zalospirone.

Where the drug is an antiemetic, it may be selected from one of the following compounds: alizapride, azasetron, benzquinamide, bromopride, buclizine, chiorpromazine, cinnarizine, clebopride, cyclizine, diphenhydramine, cliphenidol, dolasetron methanesulfonate, droperidol, granisetron, hyoscine, lorazeparn, metoclopramide, metopimazine, ondansetron, perphenazine, promethazine, prochiorperazine, scopolamine, triethylperazine, trifluoperazine, triflupromazine, trimethobenzamide, tropisetron, domeridone, and palonosetron.

Where the drug is an antihistamine, it may be selected from one of the following compounds: azatadine, brompheniramine, chiorpheniramine, clemastine, cyproheptadine, dexmedetomidine, diphenhydramine, doxylamine, hydroxyzine, cetrizine, fexofenadine, loratidine, and promethazine.

Where the drug is an antiparkinsonian drug, it may be selected one of the following compounds: amantadine, baclofen, biperiden, benztropine, orphenadrine, procyclidine, trihexyphenidyl, levodopa, carbidopa, selegiline, deprenyl, andropinirole, apomnorphine, benserazide, bromocriptine, budipine, cabergoline, dihydroergokryptine, eliprodil, eptastigmine, ergoline pramipexole, galanthamine, lazabemide, lisuride, mazindol, memantine, mofegiline, pergolike, pramipexole, propentofylline, rasagiline, remacemide, spheramine, terguride, entacapone, and tolcapone.

Where the drug is an antipsychotic, it may be selected from one of the following compounds: acetophenazine, alizapride, anperozide, benperidol, benzquinamide, bromperidol, buramate, butaperazine, carphenazine, carpipramine, chlorpromazine, chiorprothixene, clocapramine, clomacran, clopenthixol, clospirazine, clothiapine, cyanemazine, droperidol, flupenthixol, fluphenazine, fluspirilene, haloperidol, mesoridazine, metofenazate, molindrone, penfluridol, pericyazine, perphenazine, pimozide, pipamerone, piperacetazine, pipotiazine, prochiorperazine, promazine, remoxipride, sertindole, spiperone, sulpiride, thioridazine, thiothixene, trifluperidol, triflupronazine, trifluoperazine, ziprasidone, zotepine, zuclopenthixol, anisuipride, butaclamol, clozapine, melperone, olanzapine, quetiapine, and risperidone.

Where the drug is an anxiolytic, it may be selected from one of the following compounds: mecloqualone, medetomidine, metomidate, adinazolai, chiordiazepoxide, clobenzepam, flurazepam, lorazepam, loprazulam, midazolam, alpidem, alseroxion, amphenidone, azacyclonol, bromisovalum, buspirone, calcium N-carboamoylaspartate, captodiamine, capuride, carbcloral, carbromal, chloral betaine, enciprazine, flesinoxan, ipsapiraone, lesopitron, loxapine, methaqualone, methprylon, propanolol, tandospirone, trazadone, zopiclone, and zolpidem.

Where the drug is a drug for erectile dysfunction, it may be selected from one of the following compounds: Cialis (IC351), sildenafil, vardenafil, apomorphine, apomorphine diacetate, phentolamine, and yohimbine.

Where the drug is a drug for migraine headache, it may be selected from one of the following compounds: almotriptan, alperopride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

Where the drug is a drug for the treatment of alcoholism, it may be selected from one of the following compounds: naloxone, naltrexone, and disulfiram.

Where the drug is a drug suitable for the treatment of addiction, it may be buprenorphine.

Where the drug is a muscle relaxant, it may be selected from one of the following compounds: baclofen, cyclobenzaprine, orphenadrine, quinine, and tizanidine.

Where the drug is a nonsteroidal anti-inflammatory, it may be selected from one of the following compounds: aceclofenac, alminoprofen, amfenac, aminopropylon, amixetrine, benoxaprofen, bromfenac, bufexamac, carprofen, choline, salicylate, cinchophen, cinmetacin, clopriac, clometacin, diclofenac, etodolac, indoprofen, mazipredone, meclofenamate, piroxicam, pirprofen, and tolfenamate.

Where the drug is an opioid, it may be selected from one of the following compounds: alfentanil, allylprodine, alphaprodine, anileridine, benzylmorphine, bezitramide, buprenorphine, butorphanol, carbiphene, cipramadol, clonitazene, codeine, dextromoramide, dextropropoxyphene, diamorphine, dihydrocodeine, diphenoxylate, dipipanone, fentanyl, hydromorphone, L-alpha acetyl methadol, lofentanil, levorphanol, meperidine, methadone, meptazinol, metopon, morphine, nalbuphine, nalorphine, oxycodone, papaveretum, pethidine, pentazocine, phenazocine, remifentanil, sufentanil, and tramadol.

Where the drug is another analgesic, it may be selected from one of the following compounds: apazone, benzpiperylon, benzydramine, caffeine, clonixin, ethoheptazine, flupirtine, nefopam, orphenadrine, propacetamol, and propoxyphene.

Where the drug is a stimulant, it may be selected from one of the following compounds: amphetamine, brucine, caffeine, dexfenfluramine, dextroamphetamine, ephedrine, fenfluramine, mazindol, methylphenidate, pemoline, phentermine, and sibutramine.

The drug may be selected from one of the following compounds: indoles, trypamines, benzofuranes, ibogoids, ergolines, phenetylamines, substituted phenethylamines, indane derivatives, benzocyclobuten derivatives, n BOMe derivatives, NBOH derivatives, NBMD derivatives, NBF derivatives, substituted amphetamines (alpha-methyl-phenethylamines): Substituted amphetamines (alpha-methyl-phenethylamines), DOx family (2,5-dimethoxy, 4-substituted amphetamines), phenylcyclopropylamine derivatives (technically not amphetamines), substituted methylenedioxy-phenethylamines (MDxx), substituted amphetamines, cathinones, substituted cathinones, benzofuranes, substituted benzofurans, tetraline, substituted tetralins, substituted indanes, substituted napthalenes, substituted phenylisobutylamines (alpha-ethyl-phenethylamines), alpha-substituted (-alkylated) tryptamines, arylcyclohexylamines, andamantanes, diarylethylamines, morphinans, opioids, benzodiazepines, thienodiazepines, GHB, GHB analogues, methaqualone, methaqualone analogues, synthetic cannabinoids, harmaline, salvinorines, Salvinorin A, Salvinorin B, Salvinorin C, Salvinorin D, Salvinorin E, Salvinorin F, Salvinorin G, Salvinorin H, Salvinorin I, 17α-Salvinorin J, 1713-Salvinorin J, piperazines, atropine derivatives, ibotenic acid, muscimol, psilocybin, ketamin, ketamin derivatives, oxytocin, nootropics, racteams, cocaine and cocaine analogues.

These aspects may be combined in an arbitrary manner.

These and further details, advantages and features of the present invention will be described based on embodiments of the invention and by taking reference to the accompanying figures.

Figure 2:
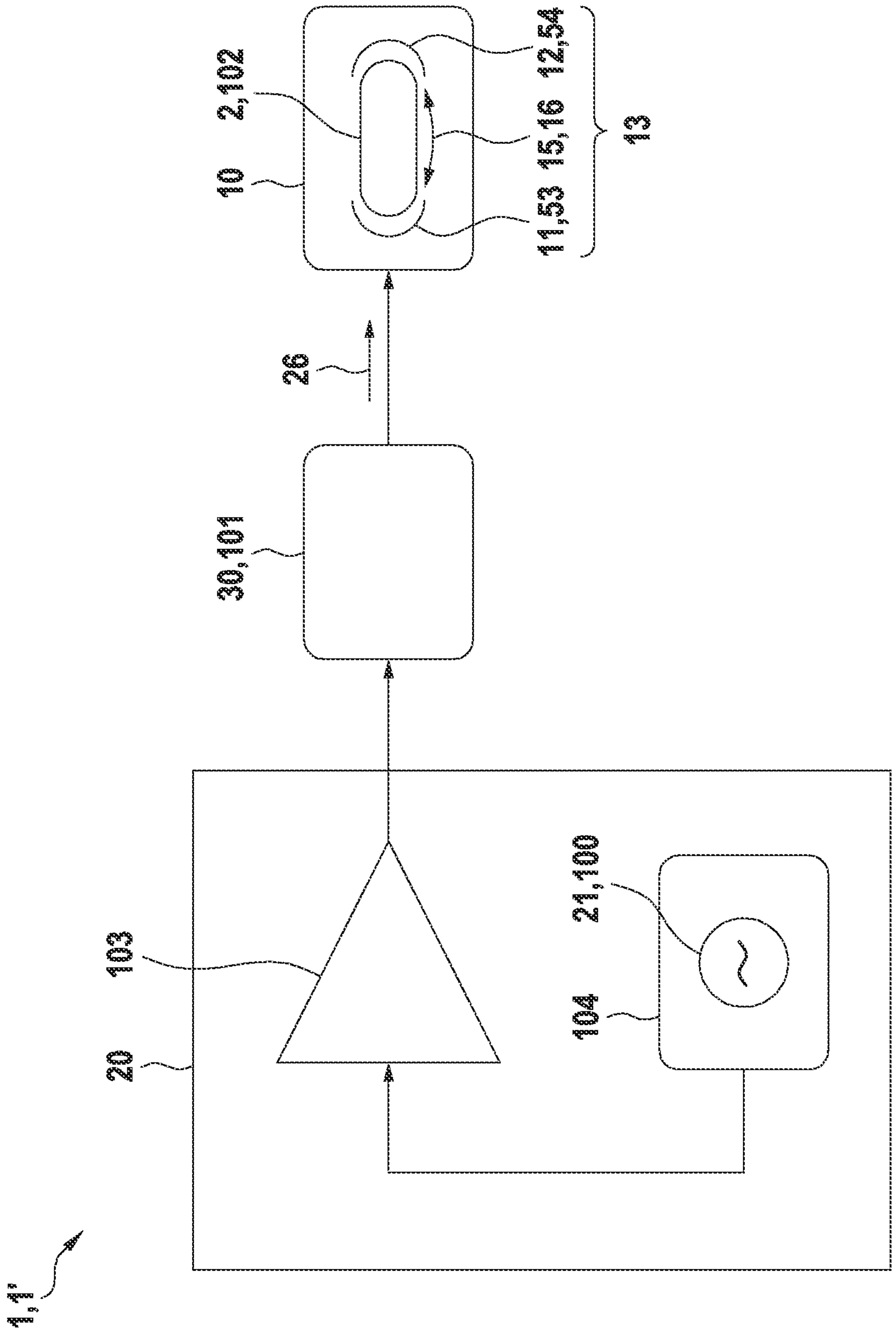
Figure 3:
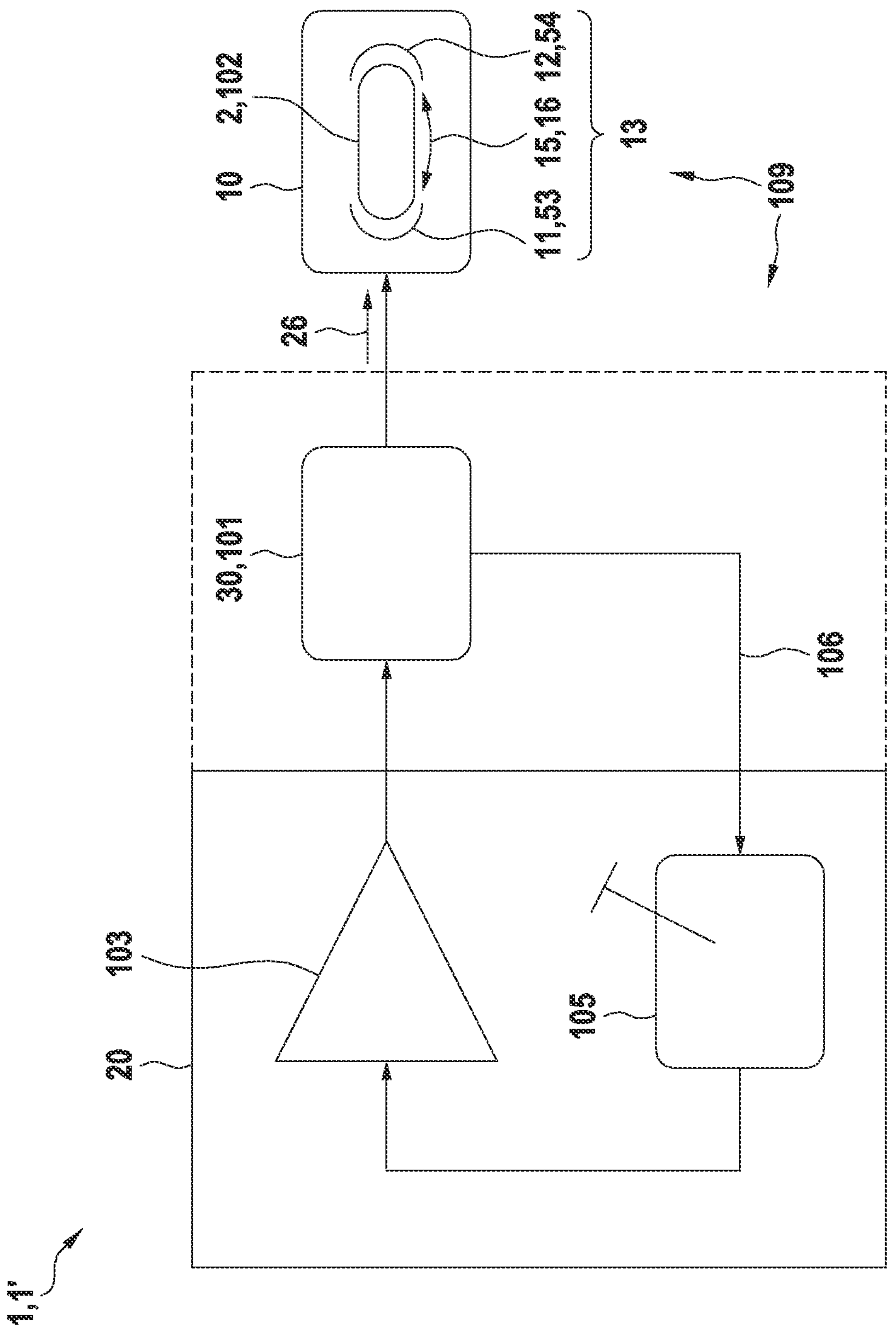
Figure 5:
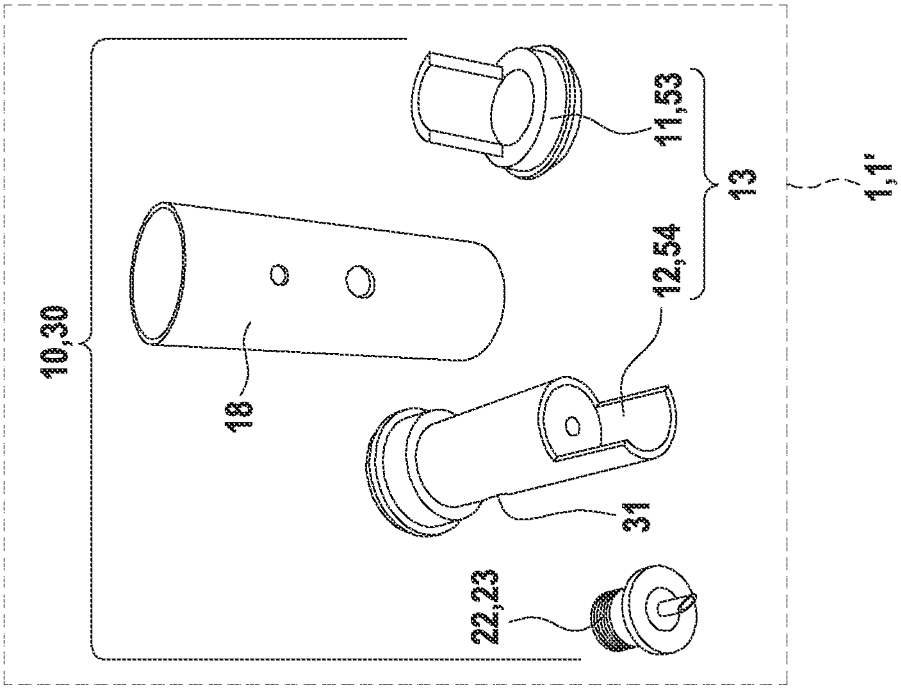
Figure 4:
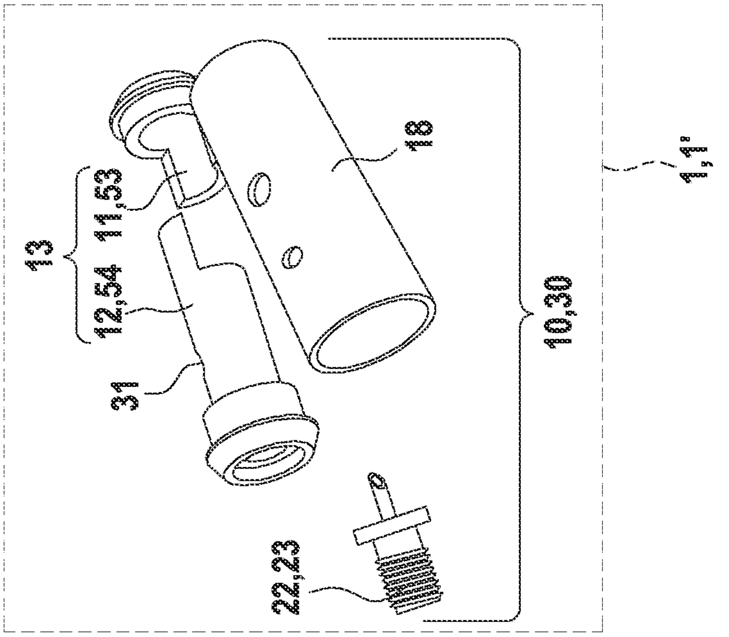
Figure 7:
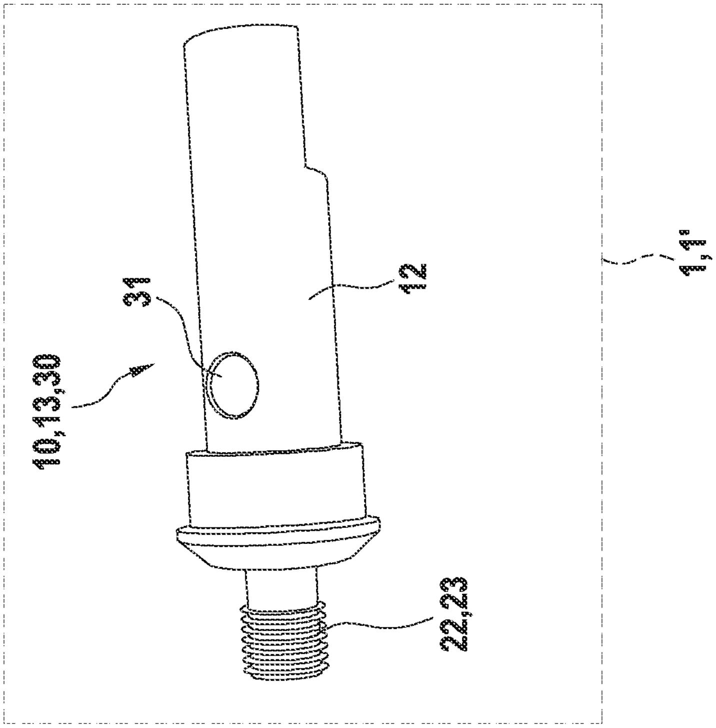
Figure 6:
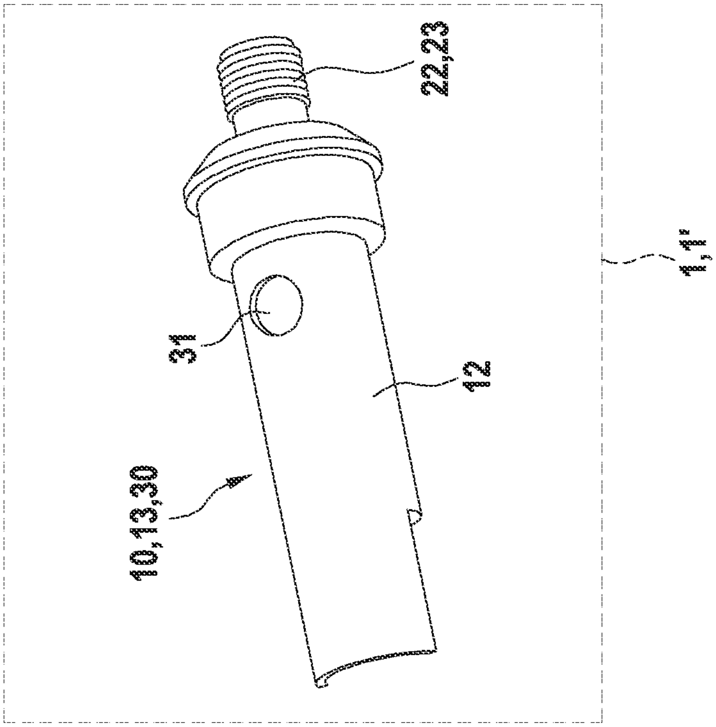

FIGS. 1 to 3 elucidate by means of schematic block diagrams preferred embodiments of the invention's microwave heating unit.

FIGS. 4 to 10C demonstrate details of preferred embodiments of the invention's microwave heating unit and its details.

FIGS. 11 to 14 explain by means of cross-sectional side views other embodiments of the invention's microwave heating unit and its details.

In the following embodiments and the technical background of the present invention are presented in detail by taking reference to accompanying FIGS. 1 to 14. Identical or equivalent elements and elements which act identically or equivalently are denoted with the same reference signs. Not in each case of their occurrence a detailed description of the elements and components is repeated.

The depicted and described features and further properties of the invention's embodiments can arbitrarily be isolated and recombined without leaving the gist of the present invention.

FIGS. 1 to 3 elucidate by means of schematic block diagrams preferred embodiments of the invention's microwave heating unit 1. Each of the microwave heating units or devices 1 shown in any of FIGS. 1 to 3 may be formed as an inhalation, vaporizer or smoking product and/or device 1', in particular for medical and/or pulmonary drug delivery/inhalation functionalities.

The embodiment of the invention's microwave heating device or unit 1 as shown in FIG. 1 is formed by or comprises a microwave radiation generating and/or releasing unit 20, which might also be referred to as a microwave radiation signal generating and/or releasing unit in the sense of the present invention. Preferably, a solid-state microwave source 100 may be used in this regard as a microwave radiation source 20.

The thereby generated and/or provided microwave radiation field can be provided to a plant/pharmaceutical containing compound/material 102 as a sample to be contained in a holding and exposing space 15, for instance a cavity 16, formed by a sample holding and exposing means 10, for instance based on first and second holding parts or holding portions 11, 12.

This is preferably done by or in cooperation with an impedance matching unit 30 configured for matching the impedance between the provided microwave radiation field and the sample holder 13 defining the holding and exposing space 15 and its cavity 16.

In this regard, impedance matching may be achieved by at least one electrical or electronic means, geometrical means and/or material means. Electrical or electronic means refer to properties of the radiation and its underlying generating and/or supplying process. Geometrical means refer to positioning, geometry and/or orientation of certain physical items. Material means refer to the positioning, geometry and/or orientation of certain material items, for instance by using a dielectric material.

In this regard an impedance matching network 101 may be involved thereby realizing the impedance matching unit 30, the network 101 realizing one of the electric/electronic geometric and/or material aspects.

In the embodiment shown in FIG. 2 and in addition to the embodiment shown in FIG. 1, the microwave radiation generating and/or the releasing unit 20 may be formed by a consecutive arrangement of a small or low power signal source 104 comprising the microwave radiation source or microwave radiation signal source 21, for instance again as a solid-state microwave (signal) source 100, and a transistor amplifier 103.

In the embodiment shown in FIG. 3 and in addition to the embodiment shown in FIG. 2, the microwave radiation generating and/or the releasing unit 20 comprises a feedback loop 106 connected between the impedance matching unit 30 and its network 101 giving input to an amplitude/phase correction device 105, with the output of which being fed into the input port of the transistor amplifier 103. Therefore, in the embodiment shown in FIG. 3 the small/low power signal source 104 substituted by the feedback loop 106 and the amplitude/phase correction device 105.

FIGS. 4 to 10C demonstrate details of preferred embodiments of the invention's microwave heating unit 1 and its details, each of which formed as an inhalation, vaporizer and/or smoking product and/or device 1', in particular for medical and/or pulmonary drug delivery/inhalation functionalities.

The invention's sample holding and exposing means 10 and the impedance matching unit 30 according to these embodiments are formed by first and second holding parts or holding portions 11 and 12 thereby defining a sample holder 13 for defining the holding and exposing space 15 by means of a cavity 16.

Essential aspects of the impedance matching unit 30 and its impedance matching network may be formed based on geometric and material aspects of the slits or slit structure 14 and in dielectric 17 used in this regard.

The sample holding and exposing means 10 may be surrounded by a housing 18 also yielding as a shield.

Figure 8B:
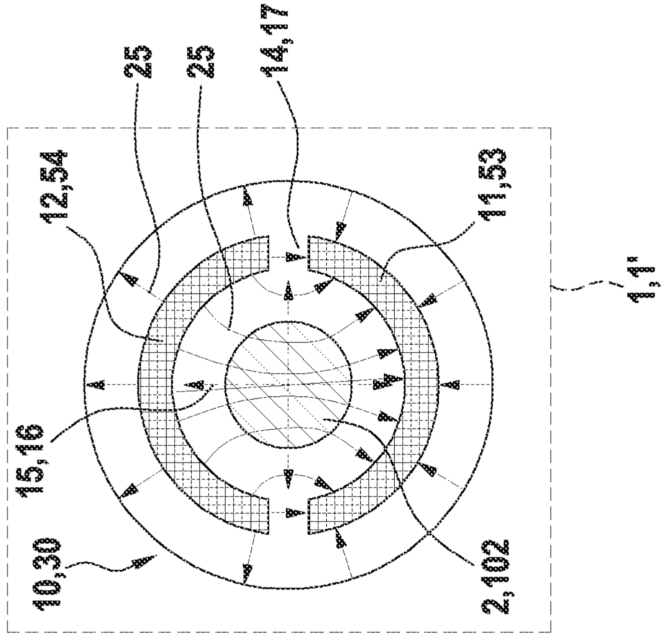
Figure 8A:
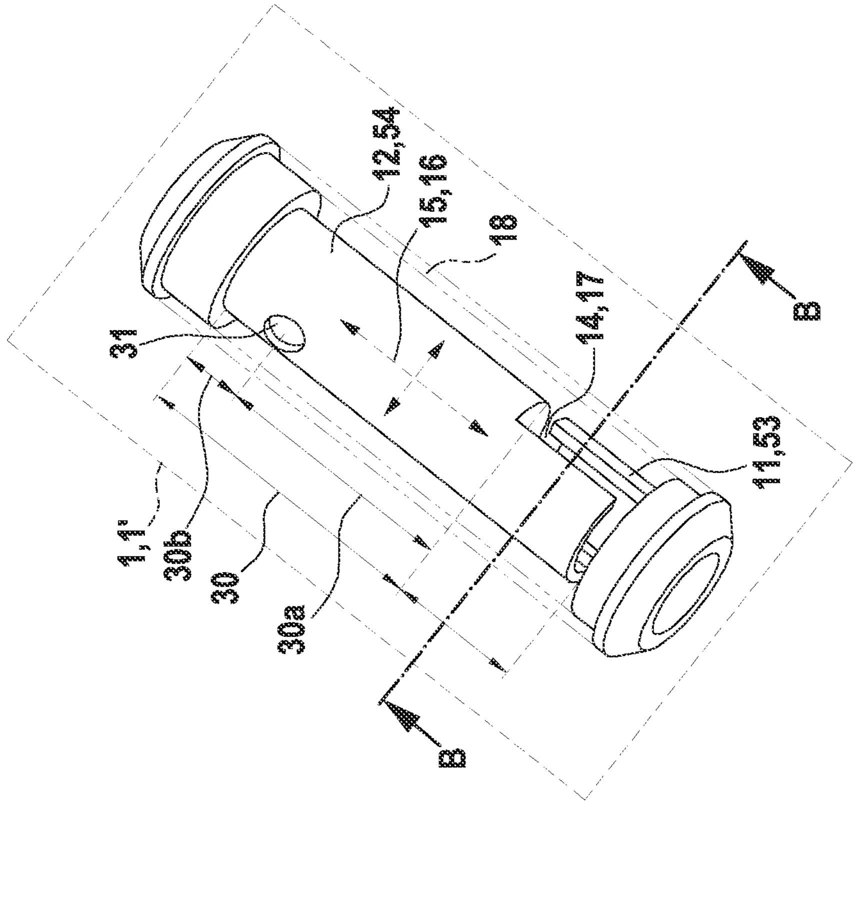
Figure 9:
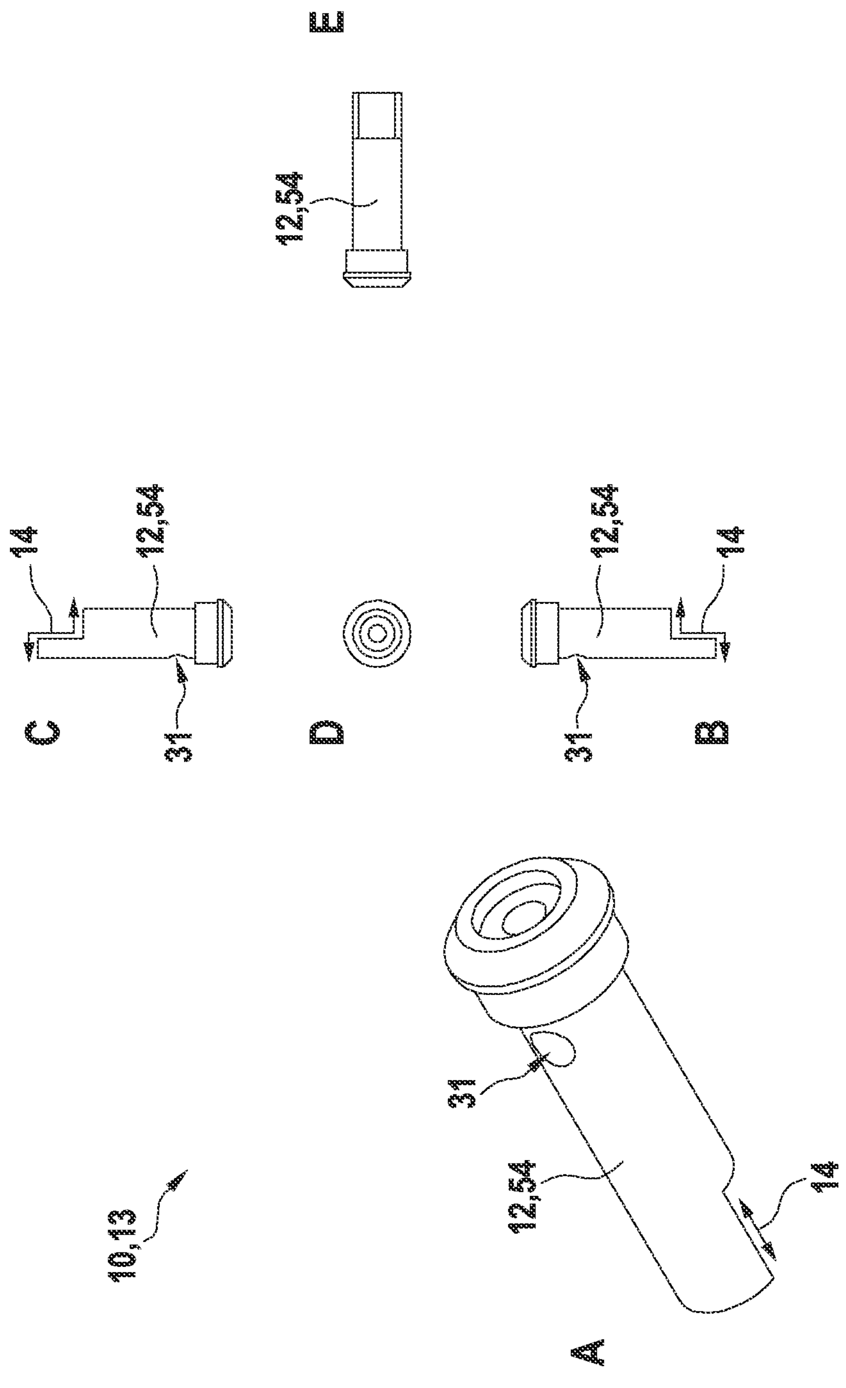
Figure 10:
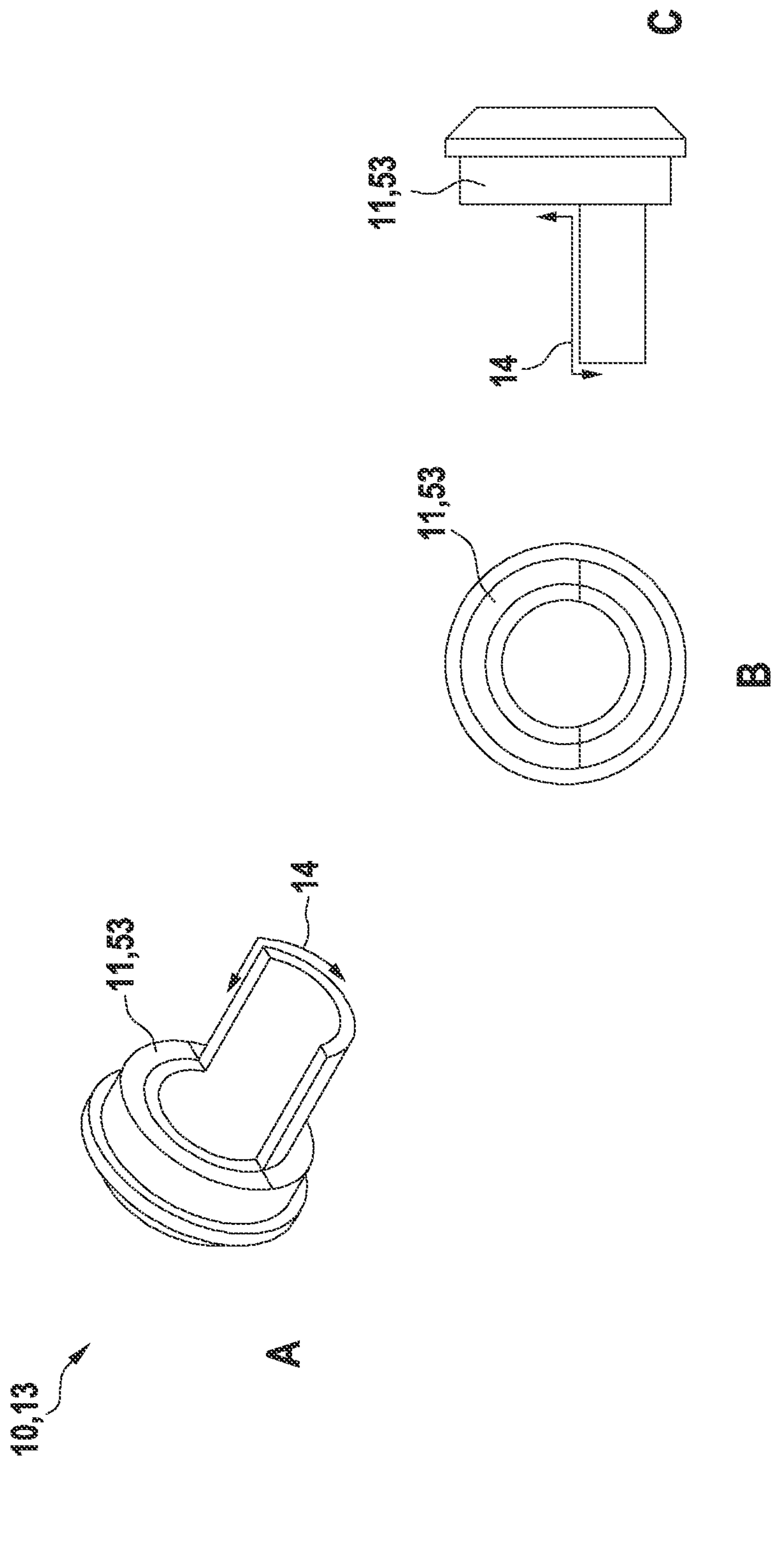
Figure 11:
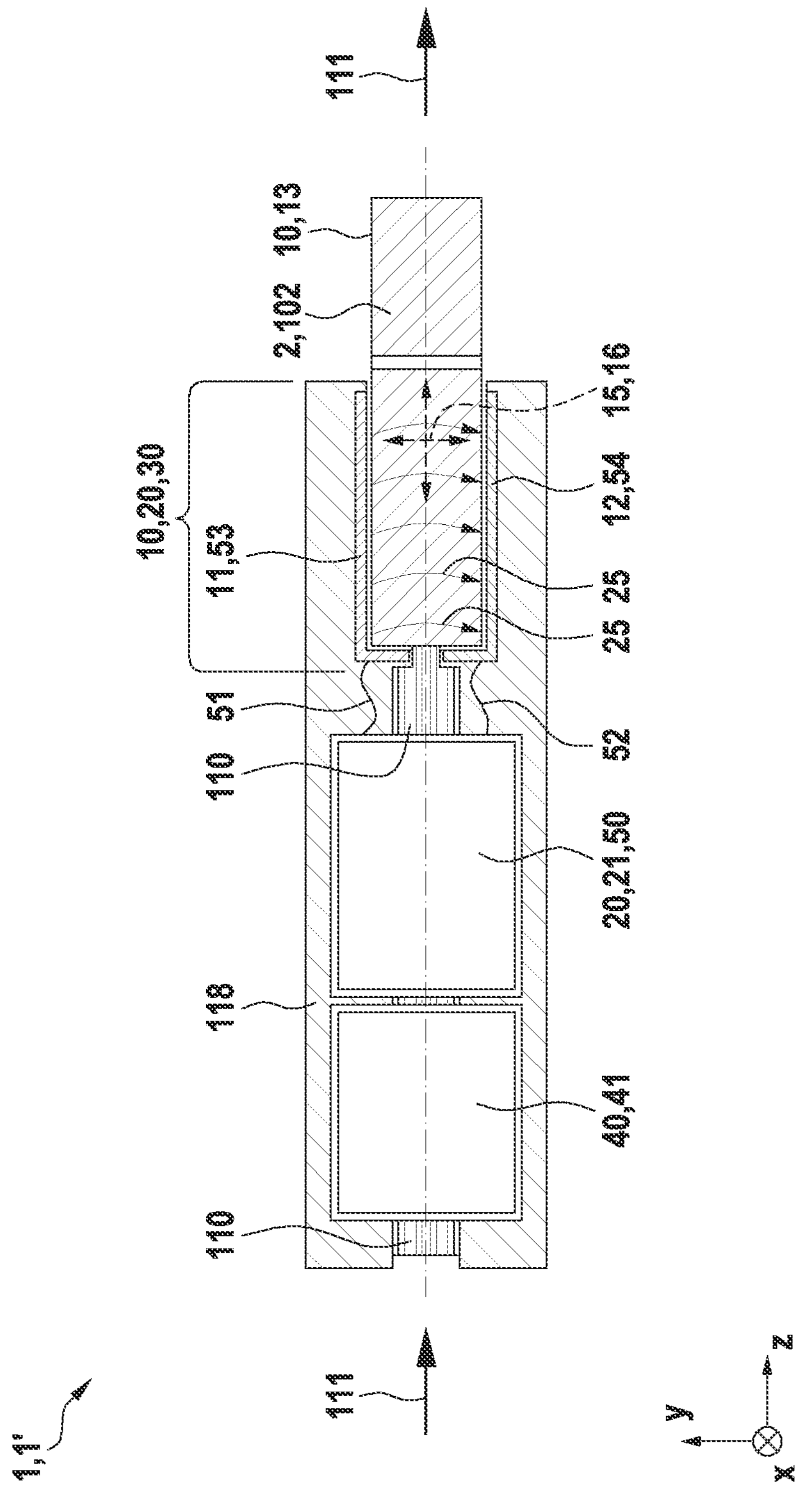

FIG. 8B elucidates—by means of a cross-sectional view along a plane B-B indicated in FIG. 8A—details of the E-field configuration of the underlying microwave radiation field 25, namely in connection with the sample holding and exposing means 10, the impedance matching unit 30 and its arrangement of the slit structure 14 and the dielectric material 17 and also in connection with the first and second holding parts/portions which may simultaneously serve as first and second electrodes 53 and 54, respectively.

As shown in FIG. 8A, the impedance matching unit 30 in one preferred embodiment may comprise a feeding portion of feeding point 31 by means of which microwave radiation may be introduced into the holding and exposing space 15 and the cavity 16. In this regard the first portion 30*a* and the second portion 30B of the sleeve component of the impedance matching unit 30 may have a length or dimension of about $\frac{1}{8}\lambda$ to about $\frac{1}{5}\lambda$ and less than $\frac{1}{10}\lambda$, wherein $\lambda$ denotes the wavelength of the underlying microwave radiation.

FIGS. 11 to 14 explain by means of cross-sectional side views other embodiments of the invention's microwave heating unit 1 and its details, each of which formed as an inhalation, vaporizer and/or smoking product and/or device 1', in particular for medical and/or pulmonary drug delivery/inhalation functionalities.

In each case of these embodiments, a power source unit 40 may be used which comprises a DC power source 40, for instance a battery, which is capable of energizing the underlying microwave radiation generating and/or releasing unit 20 with its microwave radiation source 21 and its control unit or control electronics 50 based on which and by means of first and second power supply lines 51, 52 first and second electrodes 53 and 54 are subjected to respective electric fields for generating the required microwave radiation field 25 within the cavity 16 of the holding and exposing space 15 formed in the sample holding and exposing means 10 of the sample holder 13.

By means of the microwave radiation field 25 the sample 2 with its sample material 102—in the sense of a plant/pharmaceutical containing compound or material—is heated in a fast, reliable and uniform manner to thereby release an aerosol to be conveyed with an air flow 111 entering an air flow channel 110 formed in the main body or housing 118 of the device 1'.

The sample 2 and the sample material 102 may be designed in different forms.

Figure 12:
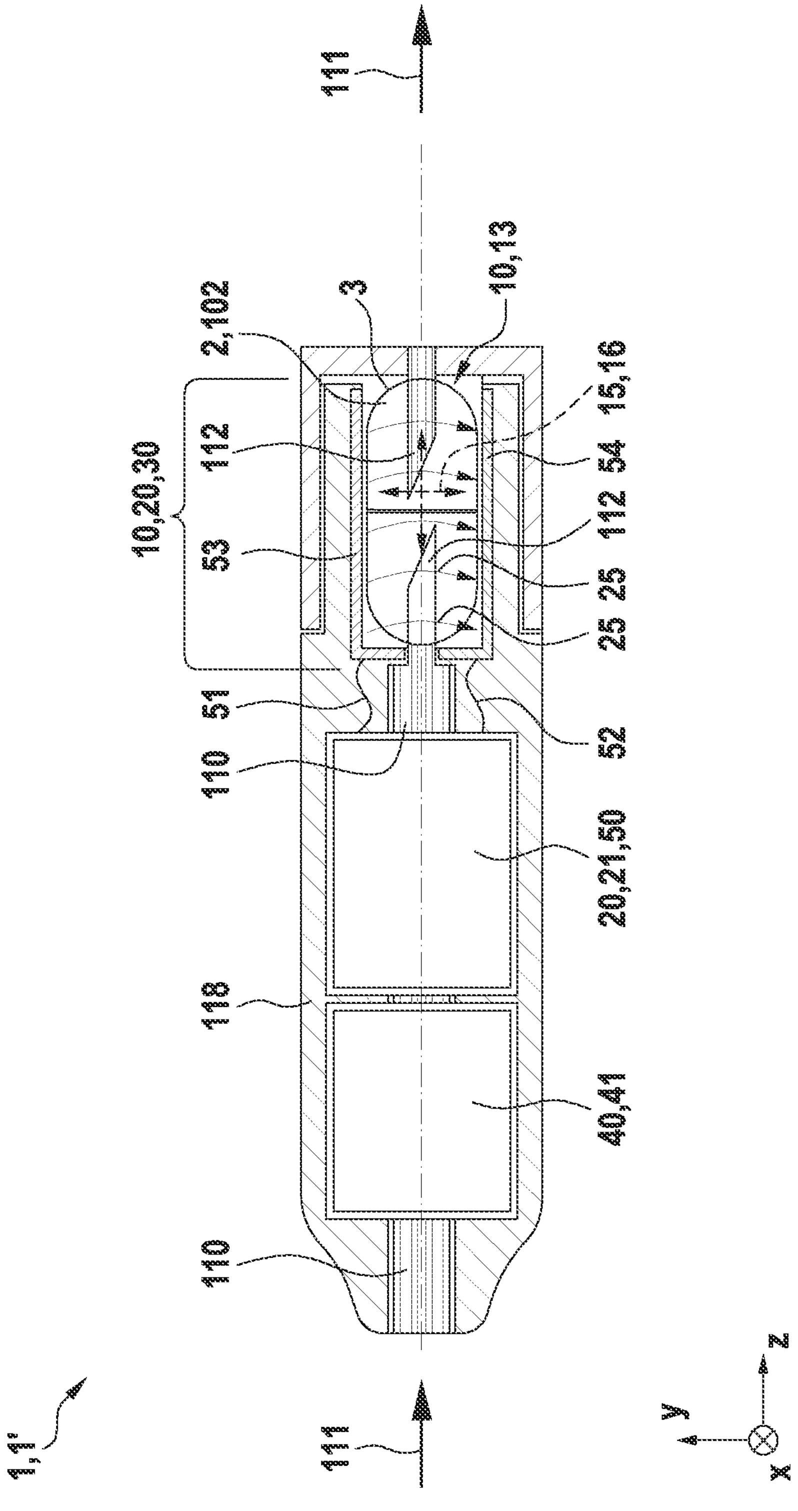
Figure 13:
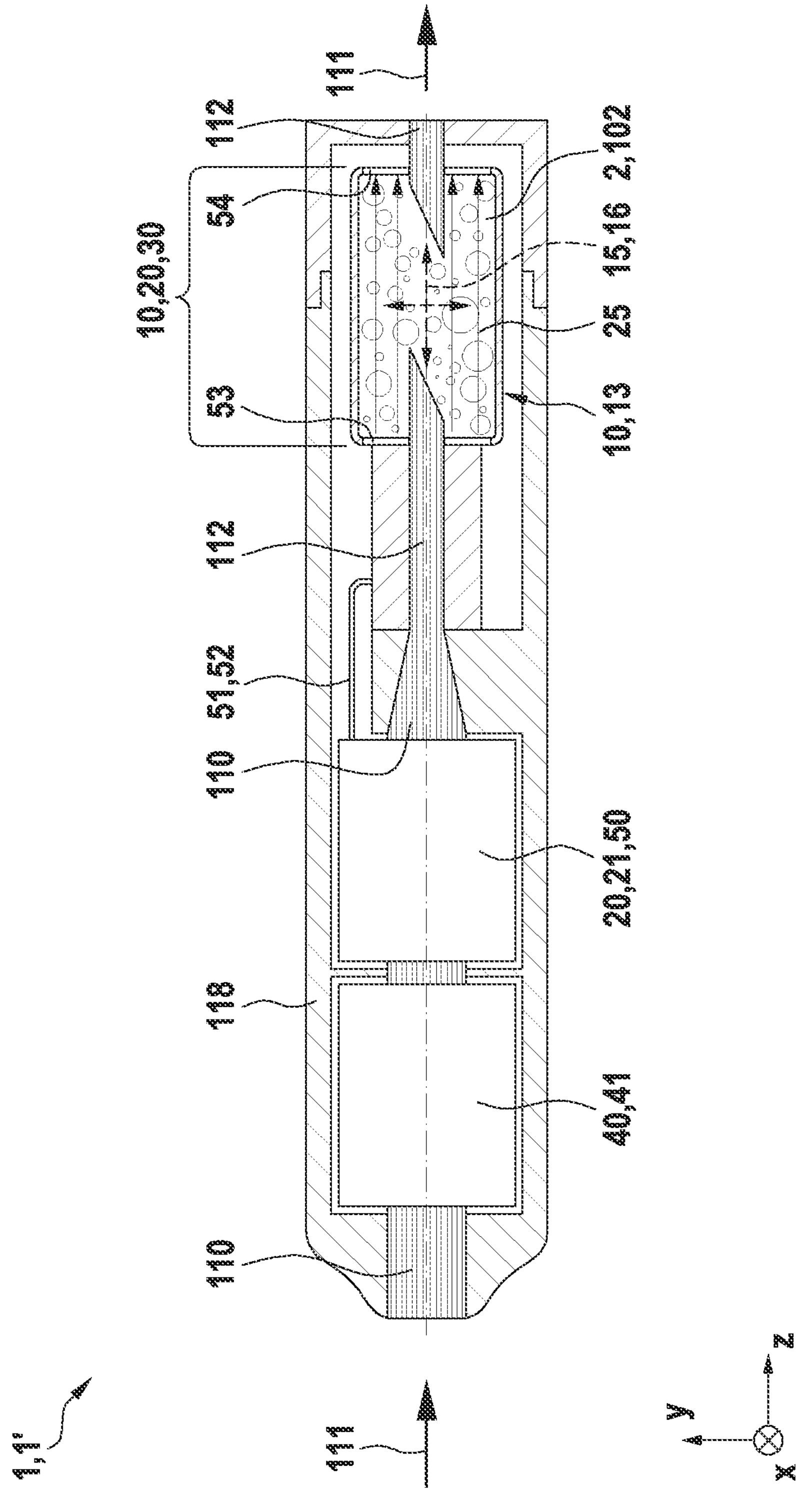
Figure 14:
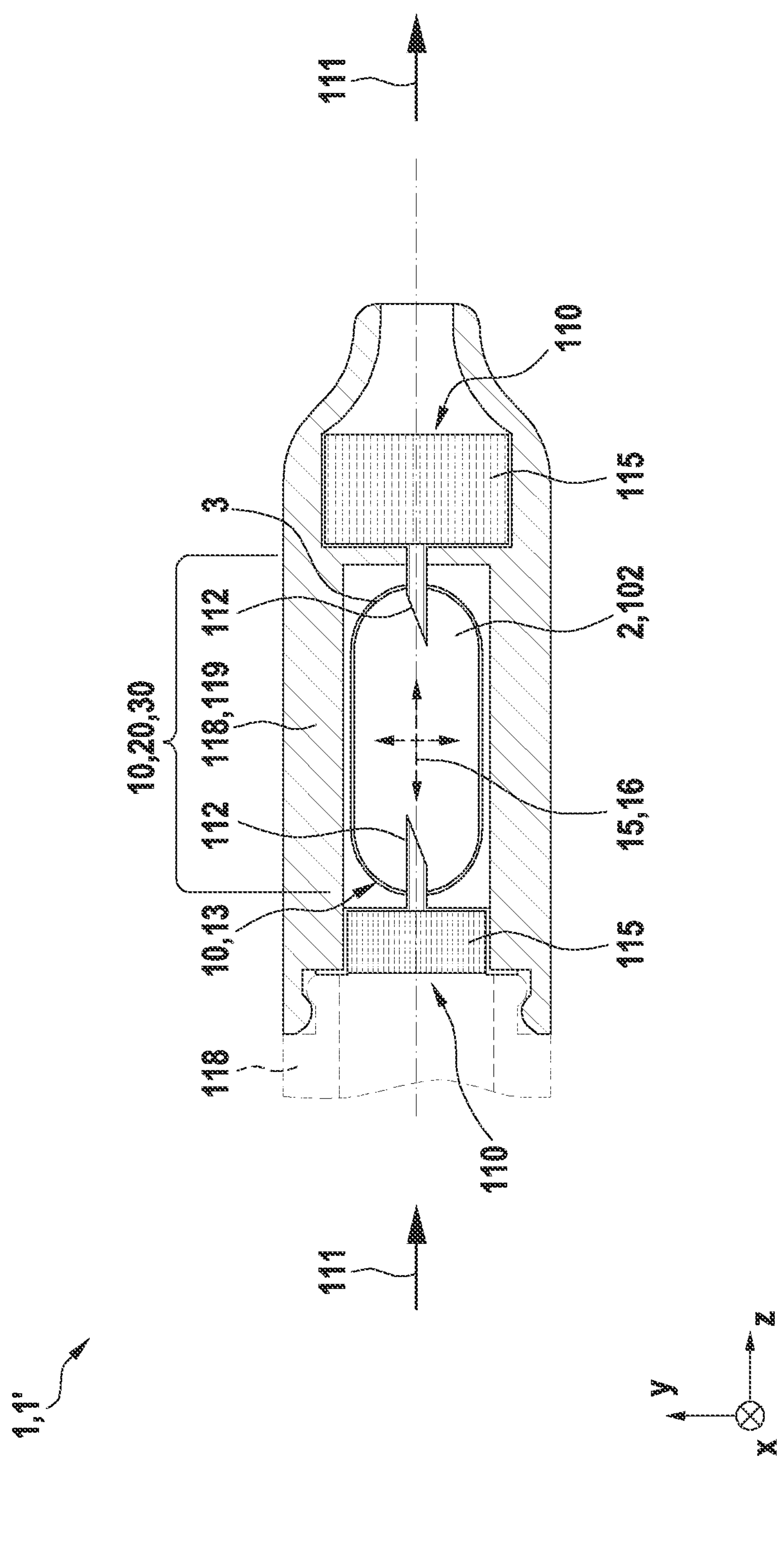

For instance, in the embodiments shown in FIGS. 12 and 14 a capsule 3 is used formed by a more or less stable wall which—upon usage—has to be penetrated by means of needles 112 or any other penetration means contained and formed in the air flow channel 110 of the device 1'.

As shown in FIG. 14, at least a part of the main body 118 or its housing 118 may be formed as a mouthpiece 119, optionally equipped with filter components 115 for interacting with the air flow 111 in the air flow channel 110.

LIST OF REFERENCE SIGNS

1 microwave heating device/unit
1' inhalation, vaporizer and/or smoking product and/or device
2 sample
10 sample holding and exposing means
11 $1^{st}$ holding part/holding portion
12 $2^{nd}$ holding part/holding portion
13 sample holder
14 slit, slit structure
15 holding and exposing space
16 cavity
17 dielectric material portion
18 housing, shield

20 microwave radiation generating and/or releasing unit, microwave radiation signal generating and/or releasing unit
21 microwave radiation source, solid-state microwave source, microwave radiation signal source, solid-state microwave signal source
22 waveguide
23 connector
25 microwave radiation field
26 microwave radiation field signal
30 impedance matching unit
30*a* first portion of impedance matching unit 30
30*b* second portion of impedance matching unit 30
31 feeding point for microwave radiation field 25
40 power source unit
41 DC power source, battery
50 control unit, electronics
51 $1^{st}$ power supply line
52 $2^{nd}$ power supply line
53 $1^{st}$ electrode
54 $2^{nd}$ electrode
100 solid-state microwave source, solid-state microwave signal source
101 impedance matching network
102 sample material, plant/pharmaceutical containing compound/material
103 transistor amplifier
104 small/low power signal source
105 amplitude/phase correction device
106 feedback loop/branch/line
109 (free running) oscillator
110 air flow channel
111 air flow
112 needle, penetration means
115 Filter
118 main body, housing
119 mouthpiece
x spatial direction
y spatial direction
z spatial direction

The invention claimed is:

1. A microwave heating unit, comprising:

(i) a sample holding and exposing unit configured to receive and hold a sample in a holding and exposing space and to expose the sample to a microwave radiation field within the holding and exposing space;

(ii) a microwave radiation unit comprising a microwave radiation source or radiation signal source, the microwave radiation unit being configured to supply the microwave radiation field and/or an underlying microwave radiation signal to the holding and exposing space; and (iii) an impedance matching unit configured to achieve impedance matching between the holding and exposing space and the underlying microwave radiation signal and/or the microwave radiation field, the impedance matching unit comprising electrodes configured for generating the microwave radiation field upon receipt of the underlying microwave radiation signal, wherein the microwave heating unit is configured for heating an aerosol-forming sample due to microwave absorption by a material of the sample thereby releasing by or from the sample upon heating the sample at least one aerosol, in or as an inhalation, vaporizer, and/or smoking product or device and/or for pulmonary drug delivery, wherein the sample holding and exposing unit comprises a sample holder defining and forming the holding and exposing space within an interior, with first and second holding portions optionally separated by a slit structure, and wherein the first and the second holding portions simultaneously serve as first and second electrodes, respectively.

2. The microwave heating unit of claim 1, further comprising a free running oscillator configured to generate and supply the microwave radiation field and/or the underlying microwave radiation signal.

3. The microwave heating unit of claim 2, wherein the free running oscillator is connected to the sample holding and exposing unit or is a part thereof, realizes an IQ modulator and/or an IQ modulator functionality, and comprises within a feedback loop a transistor amplifier, the impedance matching unit, and/or an impedance matching network, and an amplitude/phase correction device.

4. The microwave heating unit of claim 1, wherein the impedance matching unit is tunable in its matching properties concerning impedance, frequency, the aerosol-forming sample, or a combination thereof.

5. The microwave heating unit of claim 1, wherein the impedance matching unit further comprises:

the electrodes configured for generating the microwave radiation field upon receipt of the underlying microwave radiation signal, wherein the electrodes geometrically fit to the aerosol-forming sample, holding and exposing space, and/or a cavity of the holding and exposing space;

an output comprising waveguide structures, transmission lines and/or stubs;

⅛λ to ¼λ wave guide matching elements; and/or a dielectric material portion.

6. The microwave heating unit of claim 1, wherein the microwave radiation unit further comprises a connecting configuration with a connector and/or a waveguide configured to provide a connection to the microwave radiation sources, and wherein the microwave radiation source or radiation signal source is configured upon its energization to generate and/or release the underlying microwave radiation field or the underlying signal.

7. The microwave heating unit of claim 6, further comprising a power source unit configured to energize the underlying microwave radiation unit.

8. The microwave heating unit of claim 1, wherein the microwave radiation unit further comprises a transistor amplifier, and/or wherein the impedance matching unit further comprises a microwave feedback port and/or a microwave signal feedback port connected to an input of the transistor amplifier suitable to meet an underlying oscillation condition.

9. The microwave heating unit of claim 1, wherein the microwave radiation unit further comprises a transistor amplifier.

10. The microwave heating unit of claim 1, wherein the microwave heating unit is further configured as a drug delivery product and/or device, an inhalation product or device, smoking product or device, a mobile product or device, and/or a portable product or device.

11. A microwave and/or RF heating method for heating an aerosol-forming sample, the method comprising:

heating the aerosol-forming sample with the microwave heating unit of claim 1, the heating comprising microwave absorption by a material of the aerosol-forming sample thereby releasing, by or from the aerosol-forming sample upon the heating of the aerosol-forming sample, at least one aerosol comprising a phytoactive substance and/or a pharmaceutical active ingredient.

12. The method of claim 11, further comprising:

measuring and/or approximating a temperature of the aerosol-forming sample and using a value of which for controlling power supplied for energizing a microwave generation and/or releasing process.

13. The method of claim 11, wherein an operation frequency is in a range of from 1 MHz to 15 GHZ, and wherein an operation power in continuous mode is in a range from 0.1 mW to 50 Watt, or in a pulsed mode is in a range from about 0.1 mW to about 50 W, or is ramped up between a value of 0.1 W and a value of 30 W.

14. The method of claim 11, wherein the aerosol-forming sample comprises a fluid material, a solid material, a tablet, a capsule, a cartridge, a shell vial, a pellet, a pharmaceutical excipient, or a combination thereof, can be fitted according to a size of an underlying cavity, is or forms a vessel and/or has a housing, and is contained in a vessel formed as a mouthpiece configured to allow inhalation of formed aerosol, as an integral piece, as a disposal and/or to comprise a filter, and/or a hollow tube.

15. The microwave heating unit of claim 1, further comprising an impedance matching network comprising the impedance matching unit.

16. The microwave heating unit of claim 1, wherein the interior of the holding and exposing space is a cavity.

* * * * *